United States Patent [19]

McNeil et al.

[11] Patent Number: 5,888,993

[45] Date of Patent: *Mar. 30, 1999

[54] VANADIUM COMPOUNDS IN THE TREATMENT OF ELEVATED BLOOD SUGAR LEVELS

[75] Inventors: John Hugh McNeil; Chris Orvig, both of Vancouver, Canada

[73] Assignee: The University of British Columbia, Vancouver

[*] Notice: The term of this patent shall not extend beyond the expiration date of Pat. No. 5,527,790.

[21] Appl. No.: 963,240

[22] Filed: Nov. 3, 1997

Related U.S. Application Data

[60] Division of Ser. No. 480,017, Jun. 7, 1995, which is a continuation-in-part of Ser. No. 210,642, Mar. 18, 1994, Pat. No. 5,527,790, which is a continuation-in-part of Ser. No. 40,113, Mar. 30, 1993, abandoned, which is a continuation-in-part of Ser. No. 767,510, Sep. 30, 1991, Pat. No. 5,300,496, continuation-in-part of PCT/EP92/02235, Sep. 29, 1992.

[51] Int. Cl.$^6$ ......................... A61K 31/555; A61K 31/28
[52] U.S. Cl. ......................... 514/186; 514/184; 514/492; 514/884; 556/44
[58] Field of Search ..................... 514/186, 184, 514/492, 884; 556/44

[56] References Cited

U.S. PATENT DOCUMENTS

| | | | |
|---|---|---|---|
| 4,882,171 | 11/1989 | Posner et al. | 424/616 |
| 5,023,358 | 6/1991 | Lazaro et al. | 556/42 |
| 5,300,496 | 4/1994 | McNeill et al. | 514/186 |
| 5,527,790 | 6/1996 | McNeill et al. | 514/186 |

FOREIGN PATENT DOCUMENTS 2-292217  12/1990  Japan .

OTHER PUBLICATIONS

Bechmann et al., "EPR–Untersuchungen an Vanadylkomplexen," Z. Anorg. Allg. Chem., 544, 215–224 (1987).
Cantley et al (I), "Vanadate Is a Potent (Na,K)–ATPase Inhibitor Found in ATP Derived From Muscle," J. Biol. Chem., 252(21), 7421–7423 (1977).
Cantley et al. (II), "The Fate of Cytoplamic Vanadium –Implications on (Na,K)–ATPase Inhibition," J. Biol. Chem., 254(6), 1781–1784 (1979).
Habeeb et al., "Direct Electrochemical Synthesis of Some Metal Chelate Complexes," J. Coordination Chem., 8, 27–33 (1978).
Jungnickel et al., "Photometrische Bestimmung von Vanadium mit 2–Methyl–3–hydroxy–γ–pyron (Maltol)," Z. Analyt. Chem., 203, 257–260 (1964).
Kadota et al.(I), "Peroxide(s) of Vanadium: A Novel and Potent Insulin–Mimetic Agent Which Activates the Insulin Receptor Kinase," Biochem. Biophys. Res. Comm., 147(1), 259–266 (1987).
Kadota et al.(II), "Stimulation of Insulin–like Growth Factor II Receptor Binding and Insulin Receptor Kinase Activity in Rat Adipocytes," J. Biol. Chem., 262(17), 8252–8256 (1987).

Komatsu et al., "Antidiabetics Containing Vanadium Complexes," Chem. Abstr., 115, pp. 81–82, Abstr. No. 22249h (1991); see references AL and AM in the associated PTO–1449 for the corresponding patent citation.
Heyliger et al., "Effect of Vanadate on Elevated Blood Glucose and Depressed Cardiac Performance of Diabetic Rats," Science, 227, 1474–1477 (22 Mar. 1985).
Pederson et al., "Long–Term Effects of Vanadyl Treatment on Streptozocin–Induced Diabetes in Rates," Diabetes, 38(11), 1390–1395 (1989).
Ramanadham et al. (I), "Oral Vanadyl Sulfate in Treatment of Diabetes Mellitus in Rats," Am. J. Physiol., 257, H904–H911 (1989).
Ramanadham et al. (II), "Sustained Prevention of Myocardial and Metabolic Abnormalities in Diabetic Rats Following Withdrawal From Oral Vanadyl Treatment," Metabolism, 38(10), 1022–1028 (1989).
Ramanadham et al. (III), "Enhanced in vivo Sensitivity of Vanadyl–Treated Diabetic Rats to Insulin," Canadian J. Physiology and Pharmacology, 68(4), 486–491 (1990).
Ramanadham et al. (IV), "The Distribution and Half–Life for Retention of Vanadium in the Organs of Rats Orally Fed Vanadium(IV) and Vanadium(V)," Biol. Trace Elem. Res., 30(2), 119–124(1991).
Sakurai et al., "Detection of Oxovandium(IV) and Characterization of Its Ligand Environment in Subcellar Fractions of the Liver of Rats Treated with Pentavalent Vanadium (V)," Biochem. Biophys. Res. Comm., 96(1), 293–298 (1980).
Shechter et al.(I), "Insulin–Like Stimulation of Glucose Oxidation in Rat Adipocytes by Vanadyl (IV) Ions," Nature, 284, 556–558 (10 Apr. 1980).
Shechter et al.(II), "Perspectives in Diabetes –Insulin–Mimetic Effects of Vanadate –Possible Implications for Future Treatment of Diabetes," Diabetes, 39(1), 1–5 (1990).
Stewart et al., "Electron Paramagnetic Resonance Spectra of Some Oxovanadium(IV) Chelates," J. Chem. Soc., Dalton Transactions, 1972, 1661–1666.
Fisher et al., "Synthesis and Characterization of Vanadium(V) and –(IV) Hydroxamate Complexes. X–ray Crystal Structures of Oxochlorobis(benzohydroxamato)vanadium(V) and Oxoisopropoxo(N, N'–dihydroxy–N, N'–diisopropylheptanediamido)vanadium(V)," Inorganic Chem., 28(24), 4399–4406 (1989).
Matsuba et al., "Neutral Water–Soluble Indium Complexes of 3–Hydroxy–4–pyrones and 3–Hydroxy–4–pyridones," Inorganic Chem., 27(22), 3935–3939 (1988).

Primary Examiner—Marian C. Knode
Assistant Examiner—L. Eric Crane
Attorney, Agent, or Firm—Bozicevic & Reed LLP; Pamela J. Sherwood

[57] ABSTRACT

There are provided vanadium compositions for use in the treatment of hypertension, obesity and diabetes, in particular improved oral compositions comprising oxovanadium (IV) chelates of monoprotic, bidentate oxygen, oxygen and oxygen, nitrogen coordinating ligands especially kojic acid, maltol and ethyl maltol.

15 Claims, 9 Drawing Sheets

VANADIUM COMPOUNDS IN THE TREATMENT OF ELEVATED BLOOD SUGAR LEVELS

The application is a divisional of U.S. Ser. No. 08/480,017, filed Jun. 7, 1995, which is a continuation-in-part of U.S. Ser. No. 08/210,642, filed Mar. 18, 1994, now U.S. Pat. No. 5,527,790, which is a continuation-in-part of U.S. Ser. No. 08/040,113, filed Mar. 30, 1993, now abandoned, which is a continuation-in-part of U.S. Ser. No. 07/767,510, filed Sep. 30, 1991, now U.S. Pat. No. 5,300,496, and a continuation-in-part of PCT/EP92/02235, filed Sep. 29, 1992.

FIELD OF THE INVENTION

This invention relates to pharmaceutical compositions useful for lowering blood sugar, lowering blood pressure and suppressing appetite in mammals, and to a method of lowering blood glucose, treating hypertension and suppressing appetite.

BACKGROUND OF THE INVENTION

Diabetes mellitus is a mammalian condition in which the amount of glucose in the blood plasma is abnormally high. This condition can be life-threatening and high glucose levels in the blood plasma (hyperglycemia) can lead to a number of chronic diabetes syndromes, for example, atherosclerosis, microangiopathy, kidney disorders, renal failure, cardiac disease, diabetic retinopathy and other ocular disorders including blindness.

It is a disease of some complexity, as indicated by its effect on a large number of important functions of the body. There are large numbers of sufferers. For example, in the late 1980's over 2.6 million people in the United States were diabetics who were taking insulin by injection daily. Approximately an equal number of diabetics were taking oral hypoglycemic agents and another 2 to 3 million people were controlling the disease by dietary methods alone. It is estimated there are several million people in the U.S. who are undiagnosed diabetics.

In non-diabetics, plasma glucose level is maintained automatically in a complex procedure that involves, inter alia, the hormone insulin. In diabetes, external intervention is needed. Treatment of diabetics is now carried out using several drugs. Insulin is the mainstay of treatment; it replaces the natural hormone produced in the pancreas. In diabetics, insulin is not produced in sufficient quantities, or the body becomes tolerant to insulin and requires more than normal amounts to produce the necessary effect.

Insulin must be given by injection. Insulin cannot be administered orally as it is decomposed before or during passage through the gastrointestinal tract. It is difficult to determine the exact amount required. This can result in overdoses, leading to hypoglycemia, and in inadequate doses, leading to poor control of the disease and the development of secondary complications.

Oral diabetes medications (such as sulphonylureas and biguanides) are available. As with insulin it can be difficult to obtain a correct dose. There has been shown to be a difficulty with the sulphonylureas in correctly regulating blood glucose levels. Hypoglycemic episodes often occur in elderly patients. The biguanides lower blood glucose, but can produce side effects, such as lactic acidosis, which can be fatal.

Sodium orthovanadate has been found to be a potent inhibitor of $Na^+$-$K^+$ATPase. It has also been found that vanadate (vanadium (V)) taken up by the red blood cells was reduced to vanadium (IV) in the form of vanadyl ion $VO^{2+}$ in the cytoplasm. Since this work, there has been interest in the effects of vanadium, mostly as vanadate, on glucose metabolism and uptake into cells. A natural outgrowth of this work has been the study of vanadium and diabetes. (See J. Biol. Chem. 252: 7421–7423 (1977), J. Biol. Chem. 254: 1781–1784 (1979) and Diabetes 39: 1–5 (1990)).

The insulin-like effect of the vanadate ion ($VO_4^{3-}$) in vitro has been known since 1980 (see Nature 284: 556–558 (1980)) when it was shown that the insulin-like stimulation of glucose oxidation in rat adipocytes was due to the vanadyl ion. In 1985, McNeill et al. (Science 227: 1474–1477 (1985)) reported that vanadate, when administered in drinking water, decreased the elevated blood glucose and prevented the depression of cardiac performance in rats made diabetic with streptozoticin (STZ). Subsequently, there has been interest in the insulin-mimetic effects of both vanadate and vanadyl since Sakurai et al. showed that vanadate is reduced in vivo to vanadyl (Biochem. Biophys. Res. Comm. 96: 293–298 (1980)).

Vanadate however has the drawbacks that it is poorly absorbed from the gastrointestinal tract to the blood and that it is toxic. Administered concentrations must be close to the toxic level if the insulin-mimetic effects in mammals are to be achieved.

Work by McNeill et al. (see Am. J. Physiol 257: H904–H911 (1989), Metabolism 38: 1022–1028 (1989), Diabetes 38: 1390–1395 (1989) and Can. J. Physiol & Pharmacol. 68: 486–491 (1990)) has shown that vanadyl administered orally as vanadyl sulfate also lowers blood glucose and blood lipids in STZ diabetic rats and prevents secondary complications of diabetes such as cataracts and cardiac dysfunction. Vanadyl sulfate is less toxic than the vanadate form of vanadium but is also poorly absorbed. There have been attempts to modify the biological uptake of vanadium by changing the chemical form in which it is supplied from either vanadate ($VO_4^{3-}$) or vanadyl sulfate ($VOSO_4 \cdot (H_2O)_x$). In this regard, the use of various vanadate:peroxide reaction products as insulin mimics has been suggested by Posner et al. (See U.S. Pat. No. 4,882,171, U.S. Pat. No. 5,069,913 Biochem. Biophys. Res. Comm. 147: 259–266 (1987) and J. Biol. Chem. 262: 8252–8256 (1987)).

The use, for the oral treatment of diabetes, of a cysteine complex of vanadium of the formula

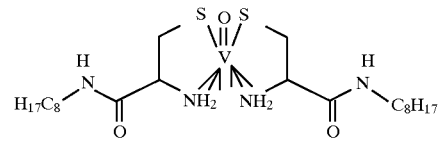

is described in EP-A-305264. The use of vanadium cysteine complexes was also reported in JP-A-2/292217 by Komatsu et al. However these cysteine complexes are generally not well characterised and only poorly water soluble and thus are not well suited to oral administration. Moreover their utility is further diminished by the relatively long delay between administration and the onset of a blood sugar lowering effect. Komatsu et al. (supra) also proposed the use of a pentane-2,4-dione complex of the vanadyl ion. This however is hydrophobic and insoluble in water and accordingly is also not well suited to oral administration.

Accordingly, there remains a need for compositions useful in the treatment of diabetes with vanadium and we have found that certain bidentate, monoprotic chelants, with vanadium co-ordinating oxygen, sulphur or nitrogen atoms form vanadium complexes particularly suitable for therapeutic use, especially for oral administration.

SUMMARY OF THE INVENTION

Thus viewed from one aspect the invention provides a pharmaceutical composition, preferably in a form adapted for administration into the gastrointestinal tract, comprising at least one physiologically acceptable carrier together with a physiologically tolerable vanadium complex of a bidentate monoprotic chelant, preferably a water-soluble chelant, capable of chelating vanadium to form a five- or six-membered unsaturated vanadium-containing ring, said ring containing at least two further heteroatoms besides vanadium, and said ring if six-membered containing vanadium-coordinating oxygen and nitrogen ring heteroatoms.

The five- or six-membered rings formed by chelation of vanadium by the bidentate monoprotic chelant used according to the invention preferably involve oxygen, sulphur or nitrogen coordination of the vanadium, particularly oxygen, oxygen or nitrogen, oxygen coordination.

DETAILED DESCRIPTION

Particularly suitably the five-membered ring forming chelants useful according to the invention may be represented by the formula I

(where
X$^1$ and X$^3$ are independently oxygen, sulphur or NX$^6$, preferably oxygen or NX$^6$;
X$^2$ is nitrogen or CX$^7$;
X$^4$, X$^5$, X$^6$ and X$^7$ are independently non-labile protons or optionally substituted alkyl, aryl, aralkyl or alkaryl or at least one pair of X$^4$ to X$^7$, preferably X$^4$ and X$^6$, together with the intervening atoms represents an optionally substituted, saturated or unsaturated homo or heterocyclic ring, or where X$^1$ represents a NX$^6$ group X$^4$ may represent a group X$^8$H where X$^8$ is oxygen or sulphur; and one X$^1$ or X$^8$ attached proton, preferably an X$^1$ attached proton, is labile).

Thus, for example, the chelant used according to the invention ay be an α-amino acid (other than cysteine), a hydroxamate or thiohydroxamate an α-hydroxy-carbonyl, such as for example an α-hydroxy-pyridinone or an α-hydroxypyrone, eg. maltol or kojic acid.

The six-membered ring forming chelants useful according to the invention preferably coordinate vanadium to form a ring carrying two fused five or six-membered homo or heterocyclic rings containing 0, 1 or 2 heteroatoms selected from O, N and S and are preferably of formula II

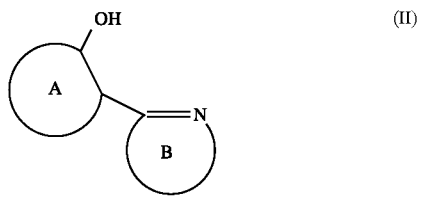

where A and B are five-, six- or seven-membered rings containing 0, 1 or 2 ring heteroatoms selected from O, N and S and optionally substituted by X$^4$ groups or oxo, thio or —NX$^4$ groups where X$^4$ is as defined above.

In formula II above, the A and B rings are preferably optionally substituted 1,2-phenylene, oxazolin-2-yl or thiazolin-2-yl groups, especially groups of formulae

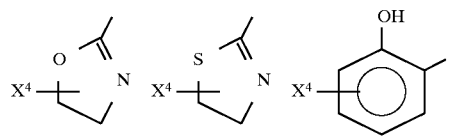

where X$^4$ is hydrogen or an optionally hydroxylated C$_{1-4}$ alkyl group.

Where the chelant comprises a homo or heterocyclic ring, unless otherwise specified this will preferably be a 5, 6 or 7 membered ring containing 0, 1, 2 or 3, especially 0, 1, or 2 heteroatoms, selected from O, N and S. Each aryl group is preferably phenyl or naphthyl, especially phenyl; each alkyl or alkenyl group or moiety preferably contains 1 to 6 carbon atoms, especially 1 to 4; and the optional substituents, which do not include thiol groups, are preferably selected from hydroxy, alkoxy, oxo, amide and amine groups, and alkyl groups carrying such substituents. Such groups may be selected for their ability to enhance the hydrophilicity or lipophilicity of the complex or to enable the complex to be conjugated to a further species, eg. a biomolecule, protein, polymer, etc.

Particularly suitable chelants of formula I and II include the hydroxamates of formula III and IV

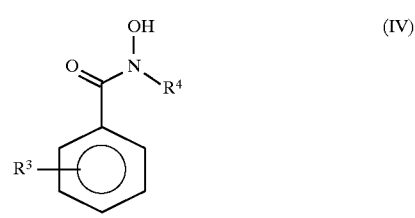

the α-hydroxy-pyridinones of formula V

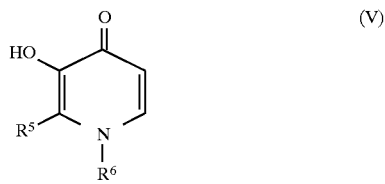

the α-hydroxypyrones of formula VI

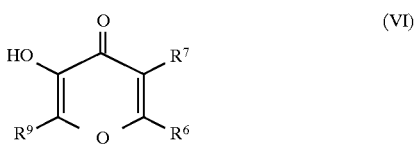

the α-amino acids of formula VII

the hydroxy carbonyls of formulae VIII and IX

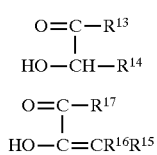

the thiohydroxamates of formulae X and XI

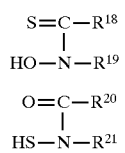

and the 2-oxazolin-2-yl-phenols and 2-thiazolin-2-yl-phenols of formulae XII and XIII

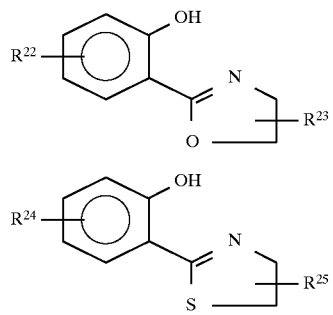

(where $R^1$ to $R^{35}$ are hydrogen or optionally substituted, e.g. hydroxylated $C_{1-4}$ alkyl).

Especially preferred as chelants of formula I are maltol, ethyl maltol and kojic acid

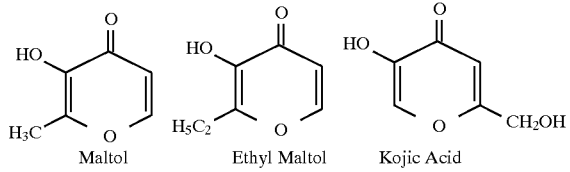

Chelants of this type are known from the literature (see for example Matsuba et al Inorg. Chem. 27: 3935–3939 (1988)) or may be produced from known starting materials by conventional techniques.

The oxazolinylphenol and thiazolinylphenol chelants are also especially preferred due to the stability to oxidation in air of the resulting vanadium complexes.

Examples of hydroxamate chelants may be found in J. Ind. Chem. Soc. 44:369–376 (1967) and Inorg. Chem. 28:4399–4406 (1989).

Thus for example many hydroxamate chelants are known. These can readily be prepared by reaction of an acyl halide with a substituted hydroxylamine

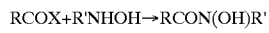

RCOX+R'NHOH→RCON(OH)R'

Many of the vanadium chelates with ligands of formula I might be prepared from maltol or maltol derivatives in a one-pot synthesis analogous to that described for gallium, aluminium and indium complexes by Zhang et al in Can. J. Chem. 67: 1708–1710 (1989). Thus

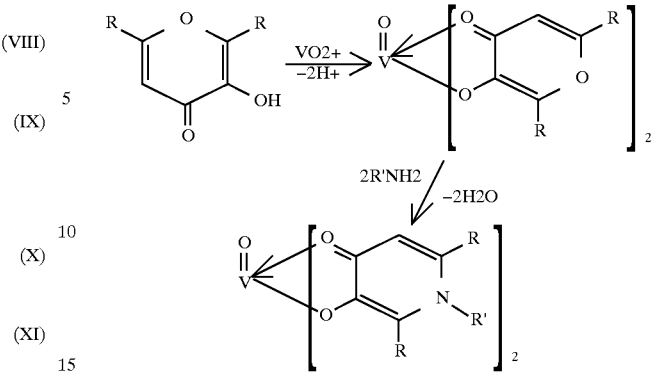

The direct electrochemical preparation of a vanadyl maltol compound was reported in J. Coord. Chem. 8: 27–33 (1978). The biological activity was not examined and the structural formula was not determined but the data suggested it to be:

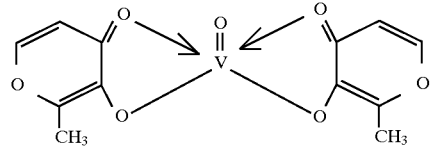

Alkoxo-oxovanadium (V) derivatives of the maltolate anion have been known since the 1960's, but again the biological activity was not examined (see Z. Anal. Chem. 203: 257–260 (1964)).

The vanadium complex used according to the invention is preferably a complex of vanadium (III), (IV) or (V), especially (IV) or (V), with a ligand as described above, especially preferably a complex $VOL_2$, $VO_2L_2$ or $VOL_2(OR^{26})$ where LH is a chelant as described above and $R^{26}$ is an optionally substituted alkyl, aryl, aralkyl or alkenyl group (where such groups are as defined above), preferably such a group is substituted by at least one hydroxyl group.

Where LH is a chelant which forms a five membered

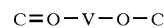

ring, these $VOL_2$ and $VOL_2(OR^{26})$ complexes, can schematically be represented by the formulae

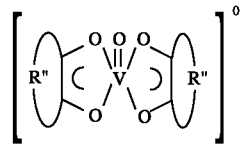

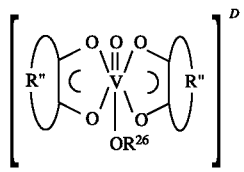

where R" is the remainder of the chelating group.

In general, backbone and ring substituents on the vanadium coordinating ligands are selected for their solubilizing effect. Desirably the vanadium complexes used according to the invention will be neutrally charged overall, water soluble (eg. capable of forming an at least 0.1 mM solution, preferably an at least 0.2 mM solution), orally absorbable (preferably with significant gastro-intestinal absorption), and have moderate to high complex stability (eg. with ligand binding constants log $\beta_2 \leq 2$ to 30, preferably 6 to 20).

Particularly preferred compounds include the maltol and kojic acid complexes bis(maltolato)oxovanadium(IV) and bis(kojato)oxovanadium(IV).

Vanadium complex formation may be effected by conventional metallation or transmetallation techniques, eg. by mixture in solution of a soluble vanadium salt with the chelant or a salt or weaker complex thereof.

We have surprisingly found that, besides being effective in the treatment of diabetes by virtue of its blood sugar lowering effect, vanadium has appetite suppressing and antihypertensive effects.

Accordingly, viewed from a further aspect, the invention provides the use of a physiologically tolerable vanadium compound, preferably a V(V) or V(IV) compound, for the manufacture of an antihypertensive or blood pressure lowering agent.

Viewed from a further aspect the invention provides the use of a physiologically tolerable vanadium compound, preferably a V(V) or V(IV) compound, for the manufacture of an appetite suppressing agent.

Viewed from a yet further aspect the invention provides a method of treatment of the human or non-human mammalian body to combat elevated blood pressure which method comprises administering to said body, for example parenterally or into the gastrointestinal tract, a physiologically tolerable vanadium compound, preferably a water soluble compound.

Viewed from a still further aspect the invention provides a method of treatment of the human or non-human mammalian body to suppress appetite, eg. for cosmetic purposes or in the treatment of illness, dysfunction or obesity, which method comprises administering to said body, for example parenterally or into the gastrointestinal tract, a physiologically tolerable vanadium compound, preferably a water soluble compound.

The vanadium compounds useful according to the invention are conveniently oxovanadium chelates but the sulphur and nitrogen analogues, i.e. VS, VEN and $VNR^{27}$ (where $R^{27}$ is as defined for $R^1$ to $R^{26}$) may also be used according to the invention in treatment to lower blood sugar, to suppress appetite or to combat hypertension.

The vanadium compounds can be given by conventional administration routes, eg. oral, rectal, intravenous, subcutaneous, intraperitoneal, transdermal, etc. However oral administration is preferred.

In the treatment of hypertension and in the appetite suppression treatment it is especially preferred that the vanadium compound be one which can be taken up by the body following administration into a body orifice, particularly oral or rectal administration, and it is especially preferred to use water-soluble vanadium (IV) or vanadium (V) compounds. While the use of the compounds described earlier for the treatment of diabetes are of course especially preferred, other physiologically tolerable inorganic salts or organic salts or complexes of vanadium can be used. In this regard reference may be made to the vanadium peroxide compositions of Posner (see U.S. Pat. No. 4,882,171 and U.S. Pat. No. 5,069,913), the vanadyl complexes of Lazaro (such as the cysteine complex Naglivan, see U.S. Pat. No. 5,023,358), vanadyl sulphate, sodium orthovanadate, vanadyl complexes with monoprotic bidentate 2,4-diones, and the vanadyl complexes of Komatsu (see JP-A-2/292217).

The invention thus also provides pharmaceutical compositions for use in the treatment of diabetes and hypertension and pharmaceutical compositions for use in suppressing appetite containing at least one physiologically acceptable vanadium source as discussed above together with at least one physiologically acceptable carrier or excipient.

The compositions for use according to the invention may be in conventional administration forms, eg. capsule, tablet, coated tablet, solution, suspension, syrup, transdermal or suppository, and conventional formulation aids and excipients may be used, eg. viscosity modifiers, buffers, flavouring agents, suspension agents, stabilizers, excess ligand, and other additives.

For transdermal administration the vanadium complexes will preferably include lipophilic and hydrophilic groups to achieve the desired water solubility and transport properties for iontophoretic administration, the vanadium complex should of course be charge neutral and the counterions will preferably be such as to generate water or an insoluble salt at the electrode.

The compositions of the invention may also contain other therapeutically active agents, eg. antidiabetic, antihypertensive and appetite suppressing agents. In this regard, special mention may be made of the metal compounds considered to be useful in the treatment of diabetes, e.g. $MgCl_2$ and chromium picolinate. Vanadium may of course be used in combination therapy with insulin, e.g. in the treatment of type I diabetes.

The combined use of vanadium and other antidiabetic agents has the advantages that the required dosages for the individual drugs would be lower and the onset and duration of effect of the different drugs would be complimentary. Thus viewed from a further aspect the invention provides a method of combined therapy of diabetes comprising administering to a diabetic mammalian subject a blood glucose lowering combination of a physiologically tolerable vanadium compound and a further antidiabetic drug.

In the combined therapy, the different active agents can be delivered together or separately, and simultaneously or at different times within the day. Moreover the compounds may be administered by any convenient and effective route, eg. by injection, orally, rectally or transdermally. Preferably administration will by orally, rectally or transdermally and also preferably the different agents will be administered substantially simultaneously, preferably as a composition containing both agents.

The combination of vanadium and other antidiabetic agents is novel and such compositions form a further aspect of the invention. Viewed from this aspect the invention provides a pharmaceutical composition comprising a physiologically tolerable vanadium compound, preferably a complex according to the invention, together with a further physiologically tolerable antidiabetic drug.

Depending on the animal and condition being treated and on the administration route the vanadium compounds will generally be administered in dosages of 0.00035 to 600 mg V/kg bodyweight per day. The range is broad since in general the efficacy of a therapeutic effect for different mammals varies widely with doses typically being 20, 30 or even 40 times smaller (per unit bodyweight) in man than in the rat. Similarly the mode of administration can have a large effect on dosage. Thus for example oral dosages in the rat may be ten times the injection dose. As a result, the preferred range for rats is 0.1 to 300 mg V/kg/day while for man it may be 0.0007 to 2.0 mg V/kg/day.

The compositions, if in solution preferably contain the vanadium compounds at concentrations which provide the effective dose either in normal daily water intake or as a daily solution supplement(s) or tablet that provides the correct dose.

The vanadium compounds will generally be administered in dosages of $10^{-5}$ to 1000 mg V/kg/day bodyweight, especially $10^{-4}$ to 500 mg V/kg/day, particularly up to 400 mg V/kg/day and most especially up to 300 mg V/kg/day. Dosages for humans by oral administration will generally lie in the range $10^{-4}$ to 2000 μg V/kg/day, preferably in the range 2.5 to 2000 μg V/kg/day, eg. 5 to 500 μg V/kg/day especially 5 to 200 μg V/kg/day and by injection in the range $10^{-4}$ to 100 mg V/kg/day, preferably in the range 0.1 to 50 μg V/kg/day, e.g. 0.25 to 50 μg V/kg/day especially 0.5 to 20 μg V/kg/day, particularly 0.7 to 20 μg V/kg/day. For rats the minimum effective doses lie generally in the ranges 10 to 30 mg V/kg for oral administration and 1 to 6 mg V/kg for injection. Thus, for example, appropriate injection dosages for rats bis(maltolato)oxovanadium(IV) may be about 15 mg/kg and appropriate oral dosages 150–300 mg/kg.

The compositions, if in solution form preferably contain the vanadium compounds at concentrations of 0.1 mM to 10M, especially 0.2 mM to 1M, particularly 1.6 to 3.2 mM.

Where the compositions are to be injected, the carrier for the vanadium compound may conveniently be aqueous methyl cellulose containing about 1% methyl cellulose.

BRIEF DESCRIPTION OF THE DRAWINGS

Efficacy of vanadium treatment according to the invention will be described below with reference to the accompanying drawings in which.

Figure 1:
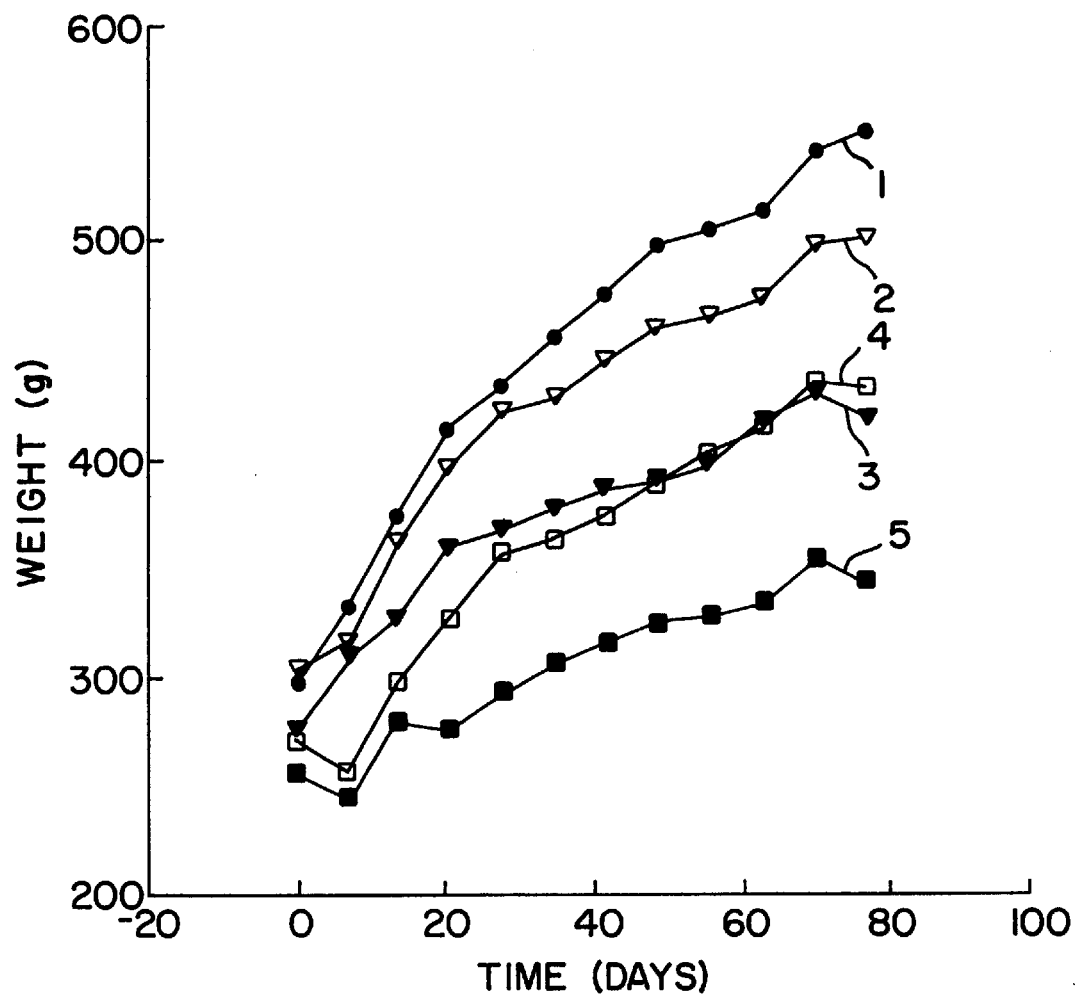
FIG. 1 relates change in weight with time.

The following non-limiting examples are provided to illustrate the invention further.

EXAMPLE 1

Bis(maltolato)oxovanadium(IV) (BMOV)

The compound bis(maltolato)oxovanadium(IV) (hereinafter BMOV) was prepared nearly quantitatively by combining maltol (3-hydroxy-2-methyl-4-pyrone) and vanadyl sulfate in hot or boiling water at a ratio of 2 to 1. The pH of the solution was raised to 8.5 and the solution was refluxed overnight. The product was a deep purple-green compound that precipitated and was filtered after cooling the reaction mixture to ambient temperature. The compound is birefringent.

The compound is characterised as follows:

Its elemental analysis is correct for $C_{12}H_{10}O_7V$; % calculated (found): C 45.45 (45.60): H 3.18 (3.30) and its electron impact mess spectrum is also consistent: m/s=317 ($M^+$). The infrared spectrum shows absorptions (KBr disk) characteristics of the maltolato anion bound to a metal cation (1610, 1570, 1465 $cm^{-1}$) and characteristic of the vanadyl group V=O (995 $cm^{-1}$). It has a magnetic moment in the solid state of 1.76 B.M. indicating one unpaired electron; however, it gives a clear $^1H$ NMR spectrum in $D_2O$ or $d_4$-methanol (δ 2.5 (s,6H), 6.55(d,2H), 8.15(d,2H)) and a clear $^{51}V$ NMR spectrum in $D_2O(-496$ ppm). The compound is quite water-soluble (about 7 mM, 2 mg $mL^{-1}$). Its log p value is 0.12.

EXAMPLE 2

Bis(kojato)oxovanadium(IV) (vanadyl kojate)

$VOSO_4.5H_2O$ (Aldrich, 2.50 g, 9.88 mmol) was dissolved in 10 mL hot water, and the solution was degassed with Ar for 10 minutes and added to 10 mL of an aqueous solution of kojic acid (2-hydroxymethyl-5-hydroxy-γ-pyrone) (Sigma, 2.88 g, 20.3 mmol) and $NaOAc.3H_2O$ (Fisher, 2.97 g, 21.8 mmol), which had also been degassed. After refluxing under Ar overnight, a blue precipitate was isolated by vacuum filtration using a Schlenk filtering funnel and dried overnight in vacuo. The yield was 2.69 g (78% based on V).

The compound is characterised as follows:

Its elemental analysis is correct for $C_{12}H_{10}O_9V$; % Calculated (found): C, 41.28 (41.06); H, 2.89 (2.89) and its fast atom bombardment mass spectrum is also consistent: m/e= 350 ($MH^+$). The infrared spectrum shows absorptions (KBr Disk) characteristic of the kojato anion bound to a metal cation (1610, 1550, 1500, 1470 ($v_{cac}$, $v_{cac}$) $cm^{-1}$) and characteristic of the vanadyl group V=O (980 $cm^{-1}$). It has a magnetic moment in the solid state of 1.76 B.M., indicating one unpaired electron. No $^1H$ NMR signal was observed in a chemical shift range from −15 to +20 ppm in a freshly prepared $D_2O$ solution. The compound is quite water-soluble (about 45 mM, 16 mg/mL). Its log p value is 0.012.

The following experiments were conducted in rats with BMOV, vanadyl kojate and vanadyl sulphate, the first two as prepared above.

EXAMPLE 3

Initial experiments were carried out to determine pharmacological effectiveness of BMOV. Using male rats, made diabetic by the injection of streptoxoticin (STZ) at a dose of 60 mg/kg i.v., BMOV was initially given by intraperitoneal (i.p.) injection as a suspension in 1% methyl cellulose.

1. Injection

Nine out of the twelve rats given 15 mg/kg i.p. (0.05 mmol/kg) responded to the compound with a decrease in blood glucose. Two animals developed hypoglycemia.

2. Oral Administration a. Drinking. Administration of the vanadyl compound in the drinking water at doses of 0.46–0.92 mmol/kg (150–300 mg/kg, using concentrations of 0.5–1.3 mg/mL) reduced blood glucose in four diabetic rats into the normal range. Fluid intake was also decreased to normal in these animals.

b. Gavage. Six out of six diabetic rats responded to the vanadyl compound with a decrease in blood glucose when BMOV was given by a single gavage treatment in a dose of 160 μmol/kg and the effects followed over 40 days. The peak fall in blood glucose occurred 5 hours after administering the drug. The blood glucose returned to diabetic levels usually within 12 hours.

Based on these preliminary studies, more detailed studies were undertaken to determine the minimum effective dose of BMOV required to maintain normal blood glucose in diabetic animals.

EXAMPLE 4

Prolonged Administration

BMOV was administered to normal and diabetic rats in drinking water.

The study was composed of 4 groups of animals Control (8 animals), Control-Treated (11 animals), Diabetic (11 animals) and Diabetic-Treated (12 animals). The diabetic state was induced by injecting STZ at 60 mg/kg dissolved in 0.9% NaCl I.V. via the tail vein to anaesthetized rats. The two control groups were injected with 0.9% NaCl I.V. through the tail vein. The diabetic state was determined with a "Testape"™ test at 3 days post-injection and later confirmed with a glucometer test. Blood glucose and insulin assays were carried out post-injection over the course of the study. Treatment according to the invention was started 1 week after determination of the diabetic state.

Treated diabetic animals received between 0.3 and 0.5 mmol/kg of the compound/day in drinking water over a 77 day period. Treated control animals received a slightly lower dose (0.2–0.3 mmol/day) over the same period. The concentration of BMOV in the drinking water was varied between 1.6 and 3.2 mM. The reason for the differing doses in the two sets of animals is that the two groups drank different amounts of water daily; it was difficult to attain the same dose in both groups.

With the above treatment regimen, the following was noted:

1. The weight gain over the 77 day period is shown in FIG. 1. As indicated above, 4 groups of animals were studied, but the diabetic-treated group was sub-divided to diabetic-treated responders (8 animals) and diabetic-treated non-responders (4 animals). Curve 1 is the control group, curve 2 the control-treated group, curve 3 the diabetic group, curve 4 is the diabetic-treated responders and curve 5 is the diabetic-treated non-responders. Initially, there was a significant difference only between the two control groups with respect to the three diabetic groups. However, by day 7 there was a significant difference between the two diabetic-treated groups with respect to all other groups. By day 28, the diabetic-treated non-responder group was significantly different from the other 4 groups and there was no longer a significant difference between the diabetic group and the diabetic responder group. By day 56, there was a significant difference between the control group and the control treated group. Treatment began with a 3.17 mM solution of the compound. On day 6, the concentration was reduced to 1.58 mM (0.5 mg/ml). On day 24, the concentration was increased to 2.37 mM (0.7 mg/ml). At this point 8 out of the 12 animals were responding to the compound.

The control treated animals showed a significantly decreased weight gain beginning at day 56. The decrease was correlated with the decrease in food intake.

Figure 2:
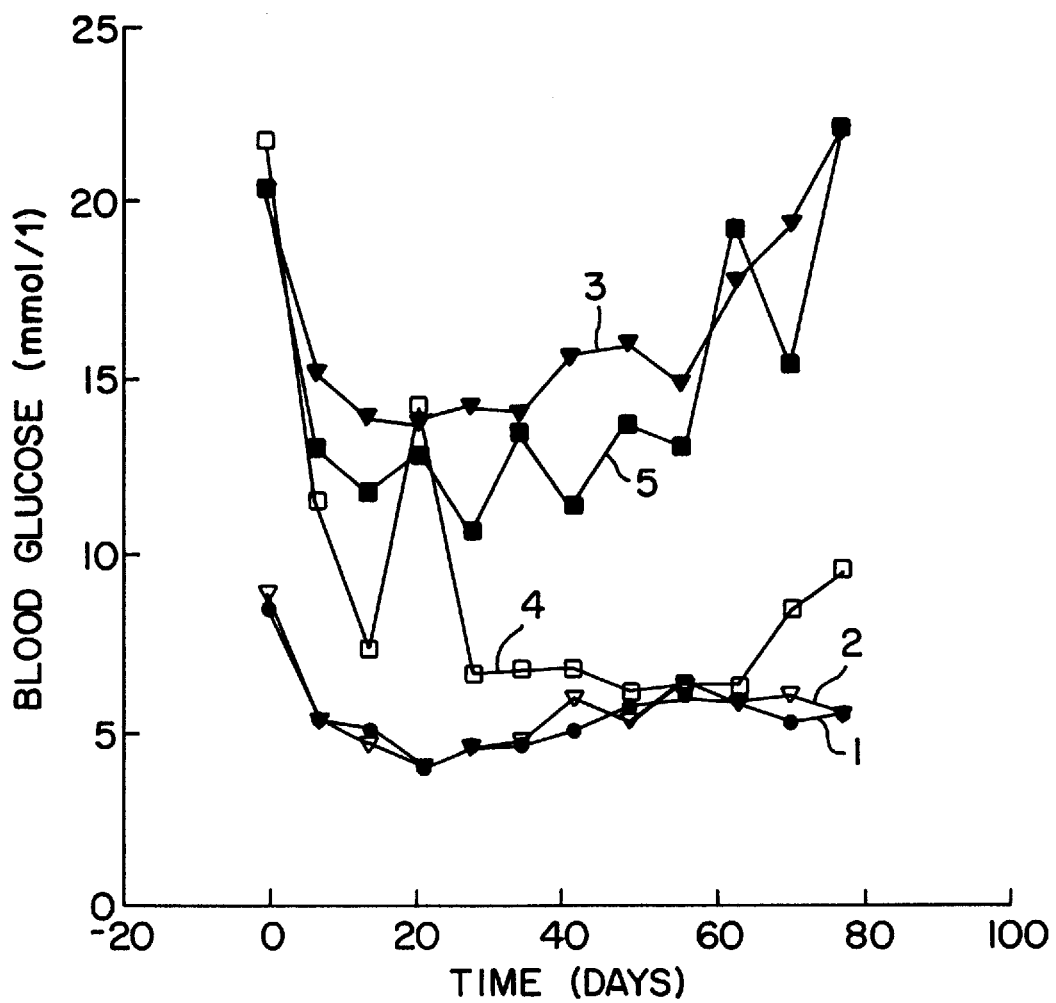
FIG. 2 shows average blood glucose values in mmol/l (over time)

2. FIG. 2 shows average blood glucose values (mmol/l) for the 5 groups based on weekly blood glucose determinations. The 5 groups were as in FIG. 1. Initially, there was a significant difference between the two control groups with respect to all three of the diabetic groups. By day 7, there was a significant difference between the diabetic group with respect to both diabetic-treated groups. By day 14, the diabetic-treated responder group was euglycemic; however, on day 18 there was an increase in blood glucose levels for this group due to the necessity to withhold treatment for a few days to treat hypoglycemia, which developed in several animals. The diabetic-treated non-responder group consists of rats which exhibited marked fluctuations in glucose values.

Thus, eight of the twelve treated diabetic rats had their blood glucose values lowered from 20°mM to less than 10 mM from day 7 onwards. Four of the twelve rats had blood glucose readings ranging from 6–30 mM on any given day. These rats are the non-responders. By day 24, diabetic rats that responded to the compound had normal blood glucose.

Figure 3:
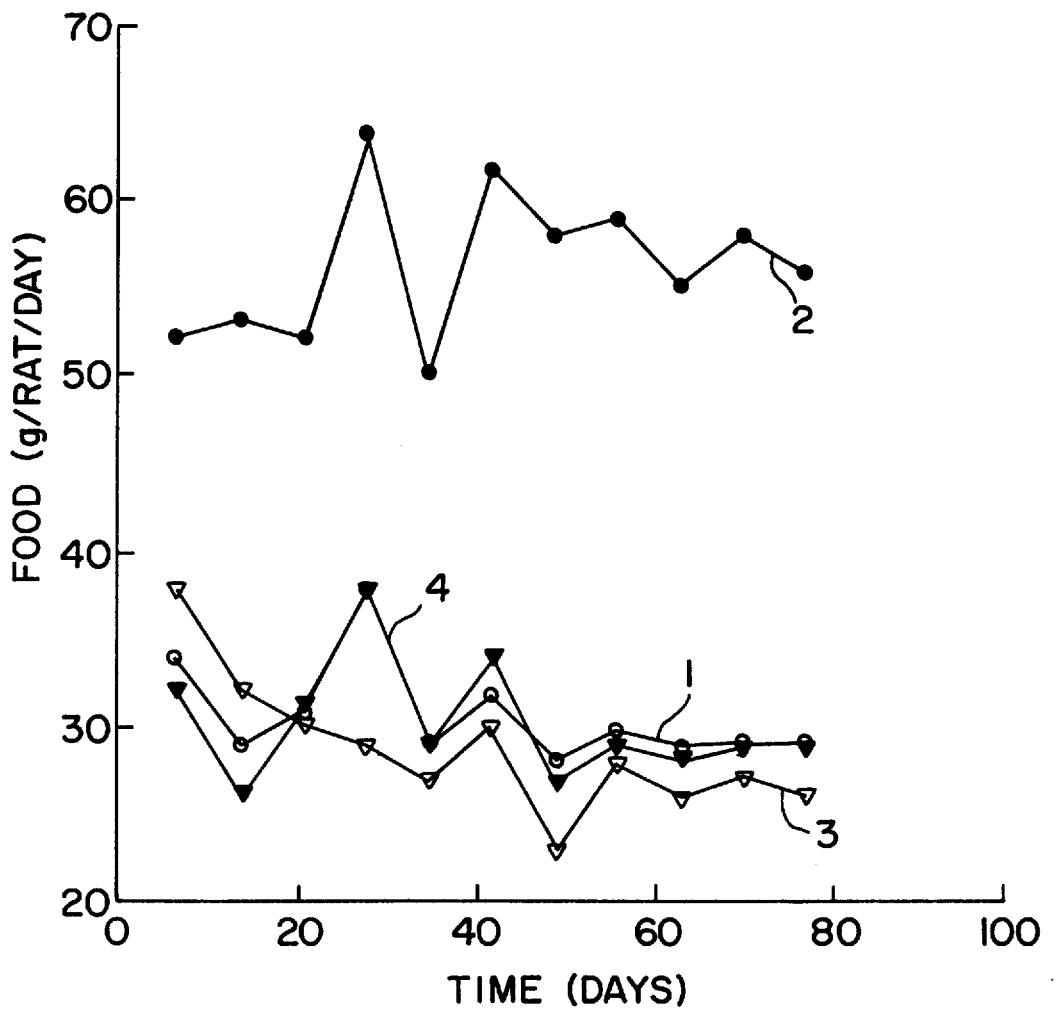
FIG. 3 shows the daily food consumption.

3. FIG. 3 demonstrates the daily food consumption per rat. The rats were allowed free access to food with 2–3 rats per cage for the four treatment groups. The control group is curve 1, the diabetic group is curve 2, the control-treated group is curve 3 and the diabetic-treated group is curve 4. For the first approximately 50 days of treatment, the only significant difference occurred between the diabetic group with respect to all of the other groups. However, from day 63 on, there was also a significant difference between the control-treated group and all the other groups. There was no significant difference between the control and the diabetic-treated groups at any time.

Figure 4:
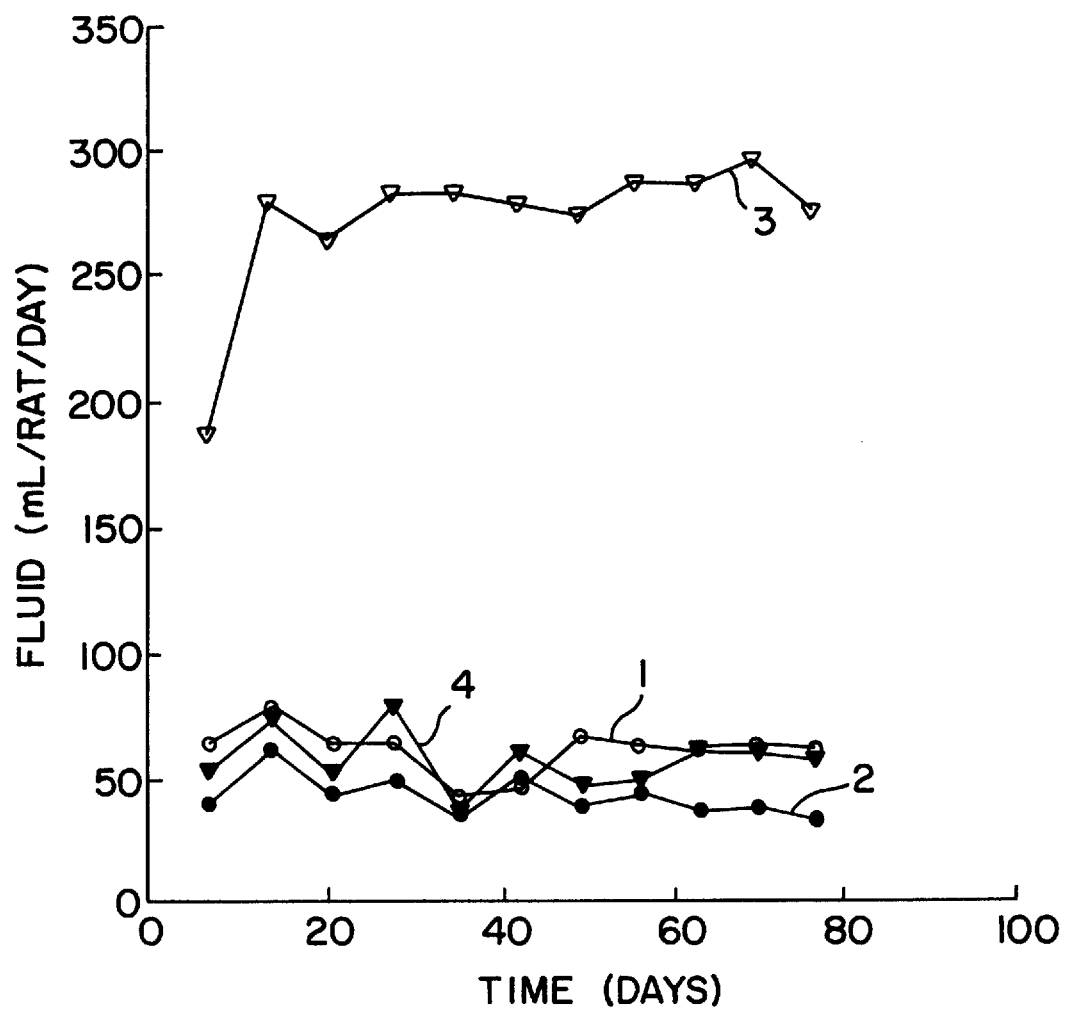
FIG. 4 shows daily fluid consumption.

FIG. 4 shows the daily fluid consumption per rat. The rats had free access to fluids with 2–3 rats per cage for the four treatment groups. The control group is curve 1, the control-treated group is curve 2, the diabetic group is curve 3 and the diabetic-treated group is curve 4. Initially, the only significant difference occurred between the diabetic group with respect to all of the other treatment groups. However by day 63, there was also a significant difference between the control treated group and all the other treatment groups. There was no significant difference in fluid consumption between the control and the diabetic-treated groups throughout.

FIGS. 3 and 4 illustrate that control of blood glucose was accompanied by a reduction in food intake in the diabetic rats from greater than 50 grams per day to about 30 grams per day (28±1.6 on day 77). There was a slight reduction in food intake (from 29±0.1 to 25.5±0.3) in control rats treated with the compound. Fluid intake fell from about 275 ml/rat in the diabetic group to about 60 ml/rat in the diabetic treated group. There was also a decrease in fluid intake in the control treated group compared with control rats (62.7±7.4 vs 33.6±7.2 ml on day 77). As stated above, the decrease in food and water intake correlates with the decrease in weight gain in control animals.

4. Treatment with BMOV decreased weight gain in control animals (200 g vs 250 g for control over the 77 day period). Diabetic-treated animals gained almost exactly the same weight (140 g) as diabetics, despite the decrease in food intake; thus weight gain in diabetic-treated animals lagged behind that of control groups animals.

5. Insulin values in control treated rats decreased to the same value as those for diabetic animals (approximately 22 $\mu$U/ml) and were significantly lower than those of control (35.8±1.2 $\mu$U/ml) as shown in Table I:

TABLE I

| Insulin Values, $\mu$U/ml (Day 28 of BMOV study) | | | |
|---|---|---|---|
| Control | Control-Treated | Diabetic | Diabetic-Treated |
| 35.8 ± 1.2 | 21.6 ± 1.2 | 21.4 ± 2.6 | 22.0 ± 1.6 |

6. Plasma triglyceride and cholesterol values in diabetic animals were restored to control values by treatment with BMOV as shown in Table II:

TABLE II

Lipid Values in BMOV Study

|  | Control | Control Treated | Diabetic-Treated Responders | Diabetic-Treated Non-Responders | Diabetic |
|---|---|---|---|---|---|
| Cholesterol mmol/l Means ± S.E.M. | | | | | |
| Pretreatment (Day before treatment started) | 1.40 ± 0.03 (8) | 1.64 ± 0.08 (11) | 1.67 ± 0.10 (7) | 1.51 ± 0.07 (4) | 1.58 ± 0.10 (11) |
| Week 6 | 1.37 ± 0.06 (8) | 1.60 ± 0.06 (10) | 1.58 ± 0.11 (8) | 1.48 ± 0.09 (4) | 2.65 ± 0.28* (11) |

*Diabetic untreated is significantly different from all other groups by ANOVA followed by either Fishers', Newman-Keuls' or Duncans' test.

| Triglyceride mmol/l Means ± S.E.M. | | | | | |
|---|---|---|---|---|---|
| Pretreatment (Day before treatment started) | 1.27 ± 0.08 (8) | 1.21 ± 0.14 (11) | 1.10 ± 0.09 (8) | 1.85 ± 0.41* (4) | 1.21 ± 0.08 (11) |

*Diabetic-treated nonresponders are significantly different from all other groups by ANOVA followed by either Fishers', Newman-Keuls' or Duncans' test.

| | | | | | |
|---|---|---|---|---|---|
| Week 6 | 1.81 ± 0.11 (8) | 2.04 ± 0.22 (10) | 1.70 ± 0.18 (8) | 2.31 ± 0.19 (4) | 4.14 ± 0.98* (11) |

*Diabetic-untreated are significantly different from all groups except diabetic-treated nonresponders by ANOVA followed by Fishers' and Duncans' test, but not by ANOVA followed by Newman-Keuls' test. One rat in this group had a very high triglyceride value - 13.1 mmol/l.

7. At the end of 77 days of treatment, 0/8 of the treated diabetic rats, which were controlled by the drug, had cataracts. 5/11 Of the untreated diabetic animals showed cataracts. One of the four treated animals, not controlled by the drug, also had a cataract. The first cataract developed at 60 days in the untreated diabetic group.

EXAMPLE 5

Comparison of BMOV and Vanadyl Kojate

Using BMOV and Vanadyl Kojate as prepared in Examples 1 and 2 above, the relative efficacy of the two compounds was assessed using rats made diabetic with STZ. Again the animals were divided into responder and non-responder groups. For a 0.063 mmol V/kg ip injection, BMOV gave a 50:50 split between responder and non-responder groups whereas for vanadyl kojate the ratio was 60:40. On oral gavage of 0.55 mmol V/kg the responder:non-responder ratios were 50:50 and 57:43 respectively (n=10). Results are presented in Table III. However over a 12 day test period, there was a 100% response in terms of blood glucose reduction for diabetic rats receiving vanadyl kojate orally. Likewise the food and fluid demand by the rats was significantly reduced.

EXAMPLE 6

Blood Pressure Reduction—Vanadyl Sulphate

The insulin resistant spontaneously hypertensive rat was used as the experiment model and the vanadyl form of vanadium as the experimental intervention. The spontaneously hypertensive rats (SHR), have been shown to be insulin resistant and hyperinsulinemic as compared to their genetic controls, the Wistar Kyoto (WKY) strain. Rats, procured at 4 weeks of age, were divided

TABLE III

Comparison of the plasma glucose levels between the acute time course experiments for BMOV (n = 8) and vanadyl kojate (N = 10)

| | BMOV | | | | Vanadyl Kojate | | | |
|---|---|---|---|---|---|---|---|---|
| | I.P. (Injection) (0.063 mmol/kg) | | oral Gavage) (0.55 mmol/kg) | | I.P. Injection (0.063 mmol/kg) | | Oral Gavage (0.55 mmol/kg) | |
| TIME (Hrs) | DTR (50%) | DTN (50%) | DTR (50%) | DTN (50%) | DTR (60%) | DTN (40%) | DTR (57%) | DTN (43%) |
| 0 | 17.51 +0.8 | 19.42 +0.15 | 18.09 +0.72 | 19.31 +0.35 | 17.94 +0.41 | 20.86 +0.28 | 15.75 +0.55 | 23.08 +1.27 |
| 1 | 14.77 +2.0 | 18.82 +0.8 | 14.55 +1.96 | 18.05 +0.46 | 14.75 +0.44 | 18.55 +0.42 | 12.5 +1.46 | 21.18 +1.45 |
| 2 | 12.65 +2.33 | 18.51 +0.79 | 13.13 +2.04 | 17.57 +0.5 | 10.17 +0.47 | 16.62 +0.65 | 10.1 +0.99 | 21.51 +1.72 |
| 4 | 10.6 +2.39 | 17.94 +0.85 | 11.68 +2.07 | 16.92 +0.35 | 9.26 +0.32 | 17.37 +0.23 | 7.96 +0.26 | 20.57 +1.07 |

TABLE III-continued

Comparison of the plasma glucose levels between the acute time course experiments for BMOV (n = 8) and vanadyl kojate (N = 10)

| | BMOV | | | | Vanadyl Kojate | | | |
|---|---|---|---|---|---|---|---|---|
| | I.P. (Injection) (0.063 mmol/kg) | | oral Gavage) (0.55 mmol/kg) | | I.P. Injection (0.063 mmol/kg) | | Oral Gavage (0.55 mmol/kg) | |
| TIME (Hrs) | DTR (50%) | DTN (50%) | DTR (50%) | DTN (50%) | DTR (60%) | DTN (40%) | DTR (57%) | DTN (43%) |
| 6 | 10.28 +1.76 | 18.08 +0.48 | 9.47 +2.58 | 16.43 +0.43 | 8.73 +0.17 | 16.62 +0.35 | 6.6 +0.35 | 18.2 +0.89 |
| 8 | 9.08 +1.06 | 17.77 +0.59 | 9.27 +2.27 | 15.02 +1.13 | 7.4 +0.12 | 15.49 +0.65 | 6.87 +0.33 | 19.06 +0.96 |
| 12 | 9.38 +0.96 | 19.07 +0.37 | 7.01 +0.57 | 17.17 +0.60 | 10.37 +0.46 | 18.24 +0.45 | 6.01 +0.25 | 18.81 +0.33 |
| 24 | 7.15 +1.51 | 19.01 +0.21 | 6.31 +0.57 | 18.07 +0.74 | 13.28 +0.83 | 18.77 +0.49 | 6.74 +0.05 | 25.0 +0.4 |

DTR - Diabetic Treated Responders
DTN - Diabetic Treated Non-responders into 4 groups: SHR (untreated), SHRV (treated), WKY (untreated), WKYV (treated). Chronic vanadyl sulfate treatment (0.75 mg/ml ad libitum in the drinking water) was started on the SHRV and WKYV groups at 5 weeks of age. After week 8, when hypertension becomes fully manifest in the SHR, weekly measurements of plasma insulin and systolic blood pressure (tail cuff method) were done on all four groups. Vanadyl, in doses of 75–125 mg/kg/day, lowered both plasma insulin and systolic blood pressure in the SHRV group at all time points from weeks 8–12 (FIG. 5), without causing any change in the plasma glucose levels. No changes were seen in the control, normotensive WKYV animals.

At week 11, the untreated control SHR and WKY groups from the prevention study were further subdivided and half the animals in each group were started on oral vanadyl sulfate treatment. This was done to observe the reversal effects of vanadyl, if any, after the SHR had become hypertensive. Vanadyl reversed hypertension in the SHR treated group (SHRV$_1$) as well as lowering their plasma insulin to control values, but had no effect in the Wistar Kyoto rats (WKYV$_1$) (see FIG. 6). A direct blood pressure reading done in all groups at termination validated the earlier indirect measurements. Vanadyl sulfate prevented as well as reversed hypertention in the hyperinsulinemic spontaneously hypertensive rat, a model that closely resembles human essential hypertension. Besides establishing further the role that insulin resistance/hyperinsulinemia may play in the development of high blood pressure, this study also indicated a possible therapeutic role for vanadyl sulfate in hypertensive, hyperinsulinemic subjects. No gastrointestinal, renal or hepatic toxicity of vanadyl was observed in the treated animals (at doses of 75–125 mg/kg/day) during the entire experimental period.

Figure 5:
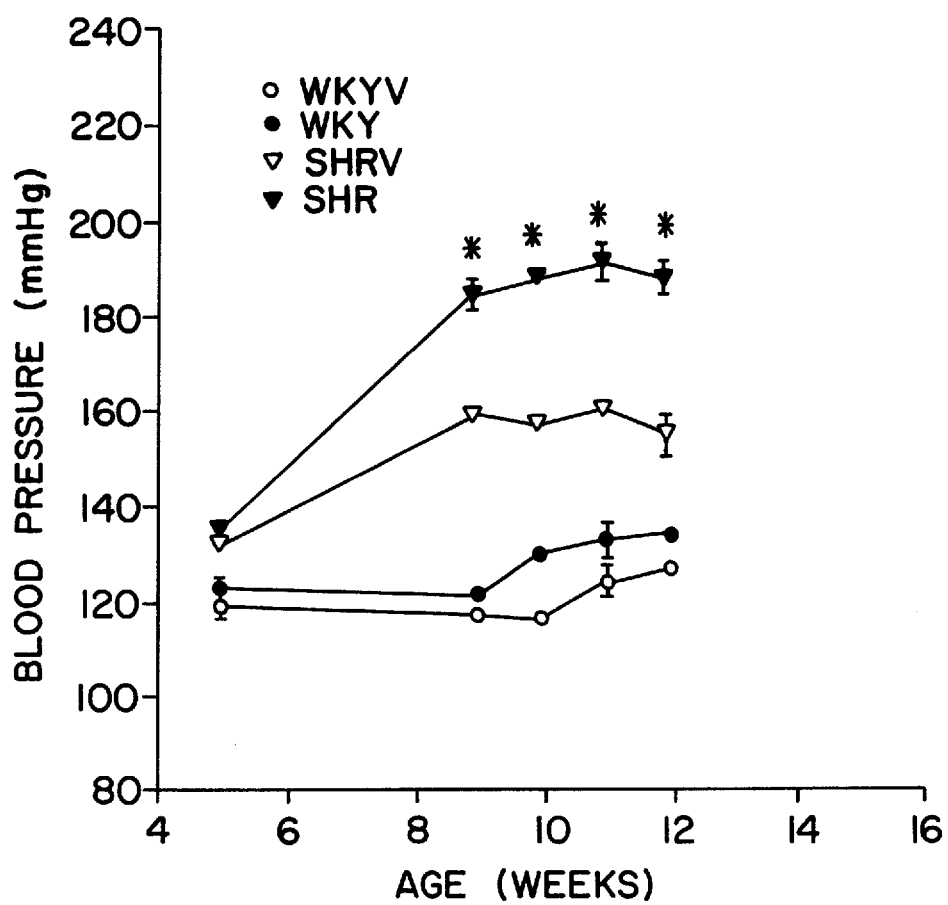
FIGS. 5 and 6 show the effects of vanadyl sulphate on blood pressure.

In summary, FIG. 5 shows that vanadyl treatment prevents the onset of hypertension in rats that normally become hypertensive during the first months of life. No change is observed in the Wistar rats which do not normally become hypertensive.

Figure 6:
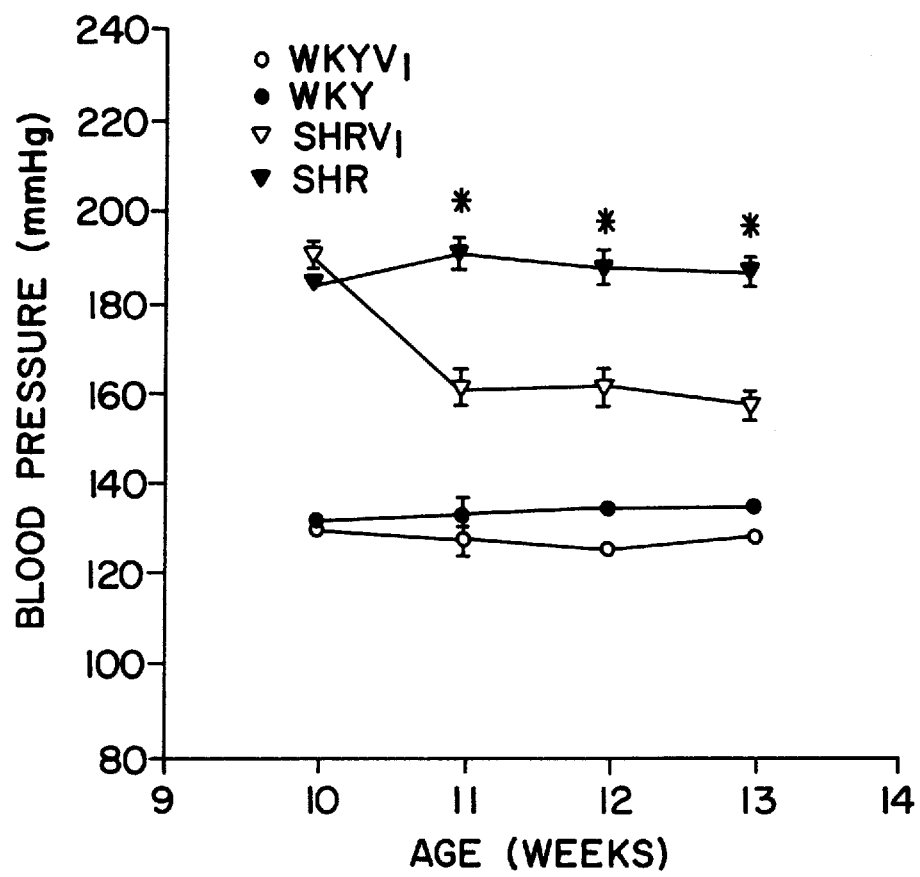

FIG. 6 shows that once SHR have been allowed to become hypertensive that the vanadyl treatment will reduce the blood pressure. Again, no effect is observed in the control Wistar rats.

The conclusion is that vanadyl is useful as a prophylactic and as a therapeutic in hypertension. Another advantage is that vanadyl has no adverse effect on normal animals (i.e. it did not produce hypotension in normal animals).

EXAMPLE 7

Blood Pressure Reduction—BMOV

11 SHR and 12 WKY rats (all male) were procured at 4 weeks of age from Charles River, Canada. The animals were divided into four experimental groups: SHR (untreated n=5), SHRO (BMOV treated n=6), WKY (untreated n=8) and WKYO (BMOV treated n=4). Chronic BMOV treatment was commenced on the SHRO and WKYO groups at 5 weeks of age. The rats were given BMOV (0.75 mg/ml) ad libitum in the drinking water. A concentration of 0.75 mg/ml was chosen since previous laboratory studies indicated that this concentration was sufficient to lower plasma insulin levels in non diabetic rats, while allowing them to gain weight at rates that were similar to untreated control animals.

Once at week 5 and then starting at week 8, weekly measurements of blood pressure were done on all groups for the next 3 weeks. Blood samples were also collected via the tail vein during the weeks mentioned above. These were centrifuged and plasma was collected for subsequent glucose and insulin analyses. Chronic blood pressure measurements were done on conscious rats, using the tail cuff method without external preheating. Initial experiments to validate the tail cuff method by comparing the readings obtained with it to those obtained by direct arterial cannulation were conducted. It was found that systolic blood pressure measured with this technique was similar to that obtained by direct arterial cannulation.

Figure 7:
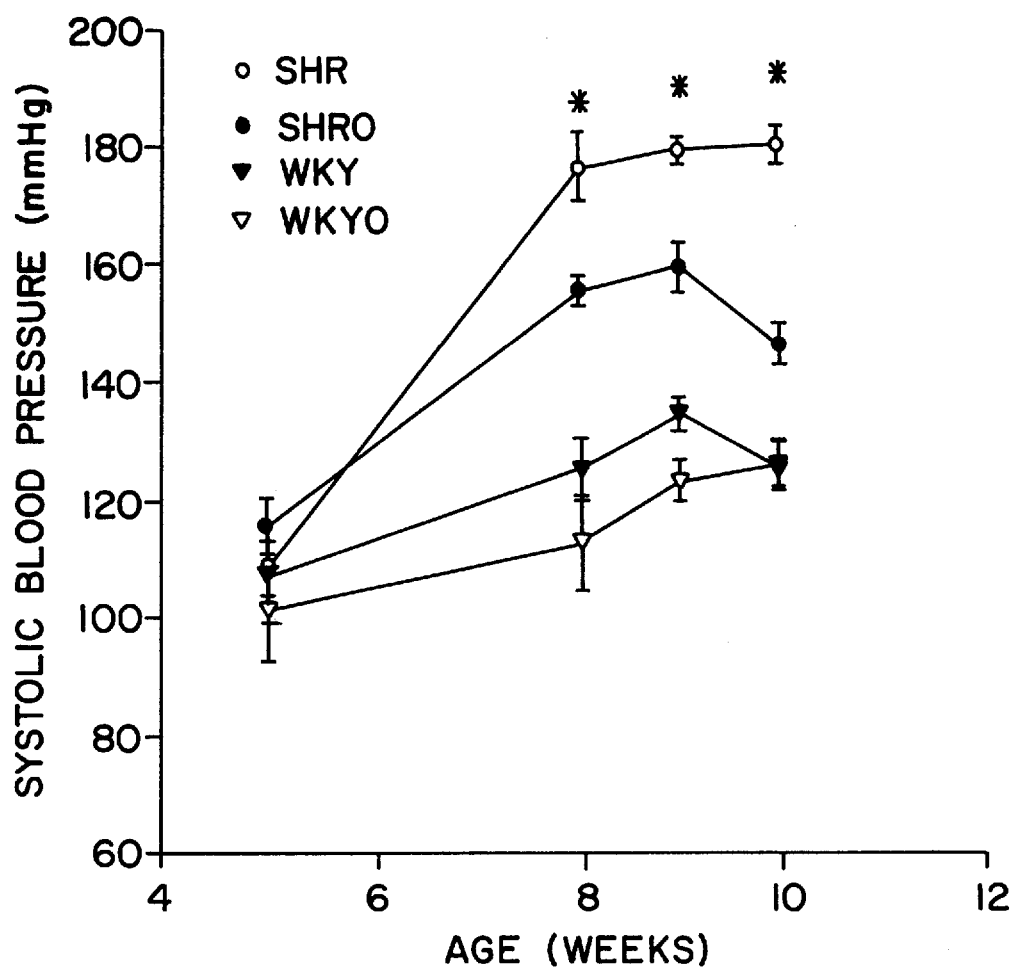
FIG. 7 shows the effect of bis(maltolato)oxovanadium (IV) on blood pressure.

BMOV caused a reduction in systolic blood pressure in the treated SHRO rats, without having any effect on the normotensive WKYO controls (FIG. 7). The decrease in systolic blood pressure after BMOV treatment was marked (25–30 mmHg) and persisted throughout the entire experimental period. Thus, BMOV was able to prevent the development of high blood pressure in the SHR.

The present invention provides a pharmaceutical composition useful for the treatment of diabetes (especially type II diabetes), as an appetite suppressant, or as an antihypertensive. The active compounds are absorbed across the gastrointestinal barrier and deliver the vanadyl ion to the bloodstream, where the insulin-mimetic properties of vanadium can be where the insulin-mimetic properties of vanadium can be expressed. In contrast to insulin, the compositions are active when taken by mouth, and represent a significant advance in diabetes therapy. The compositions are also useful as orally active appetite suppressants and would be effective in treating obesity. The majority of diabetics are overweight, but obesity in general is a significant problem in western society, leading to an increase in morbidity and mortality. Morbid obesity is a health endangering condition. A drug that will suppress appetite, leading to weight loss, is of significant value. The active ingredients of the present invention are simple, monomeric species in the solid state. They are easily prepared, easily administered, relatively stable, and highly effective in lowering blood glucose, in suppressing appetite and in combatting hypertension.

EXAMPLE 8

Bis(3-oxy-1,2-dimethyl-4-pyridinonto)oxovanadium (IV), VO(dpp)$_2$

To a solution of maltol (2.10 g, 16.7 mmol) and VOSO$_4$.5H$_2$O (2.01 g, 8.0 mmol) in 20 mL hot water was added 20 mL 40% methylamine in water (26 mmol) and the pH of the solution was decreased from 11.7 to 9.9 by addition of 2N H$_2$SO$_4$. The solution was refluxed for 8 hours. A gray blue solid was collected by filtration and washed several times with hot water. The yield was 2.56 g (94%). The solid state magnetic moment was 1.77 BM.

IR (cm$^{-1}$): 965, 1430(w), 1450, 1490, 1550, 1605

Elemental analysis: C$_{14}$H$_{16}$N$_3$O$_5$V Calc. (%): C 48.99 H 4.70 N 8.16 Found (%): C 48.56 H 4.65 N 8.38

Mass spect. (FAB): m/e=344 (HVOL$_2$$^+$, base peak), 343 (VOL$_2$$^+$)

EXAMPLE 9

Bis(2-hydroxymethyl-5-oxy-1-methyl-4-pyridinonato) oxovanadium(IV), VO(bmp)$_2$

To a solution of kojic acid (2.80 g, 19.7 mmol) in 40 ml hot water was added 20 mL 40% methylamine in water (26 mmol) and VOSO$_4$.5H$_2$O (2.47 g, 9.8 mmol) in 20 mL hot water. The pH of the solution was decreased from 12.8 to 11.0 by addition of 2N H$_3$SO$_4$. The solution was refluxed under Ar for 8 hours. A blue solid was collected by filtration and washed several times with hot water. The yield was 2.45 g (67%). The solid state magnetic moment was 1.74 BM.

IR (cm$^{-1}$): 970, 1300, 1450, 1510, 1560(m), 1610(m)

Elemental analysis: C$_{14}$H$_{16}$N$_2$O$_7$V Calc. (%): C 44.81 H 4.30 N 7.47 Found (%): C 45.00 H 4.39 N 7.47

Mass spect. (FAB): m/e=376 (HVOL$_2$$^+$, base peak), 375 (VOL$_2$$^+$)

EXAMPLE 10

Bis[2-(2'-oxyphenyl)-2-oxaxolinato]oxovanadium (IV), VO(oz)$_2$

To a solution of 2-(2'-hydroxyphenyl)-2-oxazoline (prepared according to literature) (0.31 g, 1.90 mmol) and NaOAc.3H$_2$O (0.27 g, 1.95 mmol) in CH$_3$OH (10 mL) was added VOSO$_4$.3H$_2$O (0.20 g, 0.92 mmol) in 11 mL of CH$_3$OH:H$_2$O (10:1) solution. A gray-blue solid was collected by filtration. Recrystallization of the solid from CH$_2$Cl$_2$ yielded large blue crystals. The yield was 0.27 g (75%). The solid state magnetic moment was 1.84 BM.

IR (cm$^{-1}$): 990, 1595(m), 1620(m)

UV-vis (in CH$_2$Cl$_2$) $\lambda_{max}$nm (E, M$^{-1}$cm$^{-1}$): 597 (47), 543 (45), 409 (sh, 111)

Elemental analysis: C$_{10}$H$_{16}$N$_2$O$_5$V Calc. (%): C 55.25 H 4.12 N 7.16 Found (%): C 55.12 H 4.17 N 7.08

Mass spect. (EI): m/z=391 (VOL$_2$$^+$), 229 (VOL$^+$), 163 (L$^+$)

Trans orientation of the ligands and vanadium co-ordination by the phenoxy oxygen and the oxazoline nitrogen was confirmed by X-ray crystallography at 21° C.

EXAMPLE 11

Bis[2-(2'-oxyphenyl)-2-thiazolinato]oxovanadium (IV), VO(tz)$_2$-0.5H$_2$O

The title product was prepared analogously to that of Example 10 using 2-(2'-hydroxyphenyl)-2-thiazoline (0.34 g, 1.90 mmol) (prepared according to literature), VOSO$_4$.3H$_2$O (0.20 g, 0.92 mmol) and NaOAc.3H$_2$O (0.27 g, 1.95 mmol). Recrystalization from CH$_2$Cl$_2$ yielded large yellow-green crystals. The yield was 0.32 g (82%). The solid state magnetic moment was 1.80 BM.

IR (cm$^{-1}$): 980, 1540, 1570, 1600

UV-vis (in, CH$_2$Cl$_2$) $\lambda_{max}$nm (E, M$^{-1}$cm$^{-1}$): 595(53), 537(66), 437 (sh, 179)

Elemental analysis: C$_{10}$H$_{17}$N$_2$O$_{3.5}$S$_2$V (hemi hydrate) Calc. (%): C 50.00 H 3.98 N 6.48 Found (%): C 50.42 H 3.83 N 6.47

Mass spect. (EI): m/z=423 (VOL$_2$$^+$), 245 (VOL$^+$), 179 (L$^+$)

Trans orientation of the ligands and vanadium coordination by the phenoxy oxygen and the oxazoline nitrogen was confirmed by X-ray crystallography at 21° C.

EXAMPLE 12

Bis(benzohydroxamato)oxovanadium(IV), VO(bz)$_2$

VOSO$_4$.3H$_2$O (0.20 g, 0.92 mmol) in 10 mL water was added dropwise to a solution of benzohydroxamic acid (Sigma, 0.26 g, 1.90 mmol) in 20 mL hot water. A purple solid precipitated. The pH of the suspension was raised from 1.7 to 7.4 by the slow addition of 0.5N NaOH. The suspension was then stirred for 1.5 hours. The purple solid was collected by filtration yielding 0.22 g (71%) of the product. The solid state magnetic moment was 1.72 BM.

IR (cm$^{-1}$): 995, 1440, 1480, 1510, 1570, 1600, 3200(b)

Elemental analysis: C$_{14}$H$_{12}$N$_2$O$_5$V Calc. (%): C 49.57 H 3.57 N 8.26 Found (%): C49.37 H 3.66 N 8.02

Mass spect. (FAB): m/e=340 (HVOL$_2$$^+$), 339 (VOL$_2$$^+$, base peak)

EXAMPLE 13

Bis(benzohydroxamato)methoxooxovanadium(V), VO(OCH$_3$)(bz)$_2$

VO(bz)$_2$ (0.11 g. 0.32 mmol) was dissolved in 10 mL of warm methanol (cm. 35° C.) and then stirred for 2 hours. A brick-red microcrystalline solid precipitated after the addition of 10 mL of water. The product was collected by filtration and washed several times with water. The yield was 0.065 g (54%). The solid state magnetic moment was 0.

IR (cm$^{-1}$): 960, 1440(m), 1480, 1520(b), 1600, 3200(b)

UV-vis (in methanol) $\lambda_{max}$nm (E, M$^{-1}$cm$^{-1}$): 441(2000)

$^{51}$V NMR in CH$_2$Cl$_2$ $\delta$ (ppm): −425

$^1$H NMR $\delta$ (ppm): 3.34 (3H), 7.40 (2H, J=7.5Hz), 7.49 (1H, J=7.5Hz), 7.73 (2H, J=7.1Hz)

Elemental analysis: $C_{15}H_{15}N_2O_6V$ Calc. (%): C 48.66 H 4.08 N 7.57 Found (%): C 48.46 H 4.03 N 7.54

Mass spect. (FAB): m/e=339 ($VOL_2^+$)

EXAMPLE 14

Bis(benzohydroxyamato)ethoxooxovanadium(V), $VO(OC_2H_5)$ $(bz)_2$ $VO(ba)_2$ (0.10 g. 0.30 mmol) was dissolved in 10 mL of hot ethanol and stirred for 2 hours. A golden-red solid precipitated upon slow evaporation of solvent. The product was collected by filtration and washed several times with water. The yield was 0.058 g (52%). The solid state magnetic moment was 0.

IR ($cm^{-1}$): 970, 1450, 1490, 1520(b), 1550(b), 1600, 3200(b)

UV-vis (in ethanol) $\lambda_{max}$nm (E, $M^{-1}cm^{-1}$): 446(2400)

$^{51}V$ NMR in ethanol $\delta$ (ppm): −411

$^1H$ NMR $\delta$ (ppm): 1.17 (3H, J=7.1Hz), 3.60 (2H, J=7.1Hz), 7.43 (2H, J=7.5Hz), 7.52 (1H, J=7.4Hz), 7.78 (2H, J=7.2Hz)

Elemental analysis: $C_{16}H_{17}N_2O_6V$ Calc. (%): C 50.01 H 4.46 N 7.29 Found (%): C 50.32 H 4.54 N 7.16

Mass spect. (FAB): m/e=339 ($VOL_2^+$)

EXAMPLE 15

(Comparative)

Bis(acetylacetonate)oxovanadium(IV), $VO(acec)_2$ 5 g of ammonium metavanadate ($NH_4VO_3$) was heated in a dry 250 mL beaker with constant stirring until the compound turned orange. A solution containing 12 mL $H_2O$, 9 mL concentrated $H_2SO_4$ and 25 mL ethanol was added slowly. The solution was heated, the colour changing from yellow-red to dark green-blue. It was allowed to cool slightly and was then filtered. 13 mL of acetylacetone was added to the filtrate which was then transferred to a 400 mL beaker before being neutralized by careful slow addition of 20 g $Na_2CO_3$ dissolved in 125 mL $H_2O$. The precipitate formed was removed by filtration, washed with $H_2O$, dried in air, dissolved in 50 mL dichloromethane and filtered. Anhydrous $MgSO_4$ was added to the filtered solution which was then stirred for 30 minutes, filtered and evaporated down under reduced pressure to yield $VO(acac)_2$ as a blue crystalline material.

Yield 7 g (60%).

Elemental analysis: Calc. C 45.30% H 5.32% Found C 45.31% H 5.26%

The complex shows an infrared band for $v(V=0)=1000$ $cm^{-1}$ and the magnetic moment of 1.71 BM is consistent with a single unpaired electron.

EXAMPLE 16

(Comparative)

Bis(salicylaldehyde)oxovanadium(IV), $VO(Sal)_2$

Methanol, ethanol and water were degassed by being vigorously stirred for 15–20 minutes while argon was bubbled through. Under a flow or argon, 6.1 g of salicylaldehyde was dissolved in 50 mL of degassed methanol. 5.425 g of vanadyl sulphate trihydrate ($VOSO_4.3H_2O$) was dissolved in 25 mL degassed water and 25 mL degassed ethanol. The resultant blue solution was added to the colourless salicyladehyde solution to give a green solution which was stirred at 5° C. for three days. 10 g of anhydrous sodium acetate was added under argon resulting in a rapid colour change from emerald green to yellow-brown. This solution was stirred at 5° C. for a further two days by which time a yellow-green precipitate had formed. The precipitate was removed by filtration, washed with water (3×10 mL) and then diethylether (4×15 mL) and dried under reduced pressure. The yield was 4.4 g (60%).

Elemental analysis: Calc. ($VO(Sal)_2$) C 54.39% H 3.26% Calc. ($VO(Sal)_2.H_2O$) C 48.71% H 3.70% Found C 41.60% H 3.40%

Repeated performance of the preparation gave similar elemental analysis results.

The complex showed an infrared band $v(V=0)=960$ $cm^{-1}$.

EXAMPLE 17

Comparative Testing

Six male wistar rats weighing between 175–200 g were obtained from a local source. Diabetes was induced in all animals by a single intravenous injection of streptozotocin (STZ) 60 mg/kg in 0.9% NaCl via the tail vein. Three days after STZ injection, blood was collected from the tail by nicking the tail tip and expressing the blood into heparinized capillary tubes. Blood was centrifuged at 20,000 g for 10 minutes to separate the plasma. Glucose analysis was done immediately on the plasma sample using a Boehringer Mannheim kit. Plasma glucose levels greater than 13 mM were taken as diabetic. One week after STZ injection animals were randomly divided into 3 pairs of rats. Each pair of rats received by oral gavage 1 mmol/kg of BMOV or $VO(Sal)_2$ or $VO(acac)_2$, suspended in 3% acacia. Blood was collected for plasma glucose analysis as described above immediately prior to dosing and at 2, 4, 6, 8, 12 and 24 hours after administration.

The plasma glucose levels (mM) detected for the three test complexes are set out in the Table below

| Drug | Rat | Time (Hours) | | | | | | |
|---|---|---|---|---|---|---|---|---|
| | | 0 | 2 | 4 | 6 | 8 | 12 | 24 |
| $VO(Sal)_2$ | 1 | 21.09 | 22.77 | 20.18 | 20.67 | 21.57 | 19.24 | 18.73 |
| | 2 | 21.12 | 22.31 | 21.74 | 21.85 | 21.59 | 19.74 | 18.64 |
| BMOV | 3 | 23.02 | 23.87 | 22.27 | 21.21 | 20.26 | 9.97 | 0.8 |
| | 4 | 23.01 | 23.15 | 23.32 | 22.09 | 19.45 | 8.73 | 1.0 |
| $VO(acac)_2$ | 5 | 23.87 | 22.91 | 22.37 | 23.96 | 27.19 | 19.13 | dead |
| | 6 | 22.74 | 24.5 | 22.89 | 22.94 | 23.65 | 18.86 | 2.43 |

The normal glucose level for a healthy rat is about 5–6 mM, a level of about 13 mM would be considered diabetic and the normal range for STZ diabetic rats is 20–25 mM.

The high gavage dosage of 1 mmol/kg selected for the comparison was selected to enable any blood sugar lowering effect of the compounds of Comparative Examples 15 and 16 to be detected. For BMOV the preferred dosage to achieve englycermia would have been 0.55 mmol/kg.

From the results set forth in the Table above it is immediately clear that BMOV is superior in blood glucose reducing effect to the compounds of Comparative Examples 15 and 16.

EXAMPLE 18

Ammonium bis(maltolato)dioxovanadate

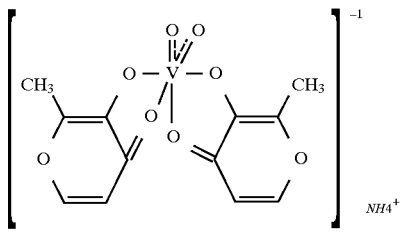

One equivalent of ammonium vanadate was dissolved in water. Two equivalents of maltol were added and the mixture was allowed to stir overnight. During this time yellow microcrystals formed. They were filtered and dried. An 87% yield of ammonium salt of bis(maltolato)dioxovanadate was obtained. Elemental, spectral, and x-ray analysis confirmed the composition and structure.

EXAMPLE 19

Six male Wistar rats, weighing 175–200 gm, were made diabetic by the intravenous injection of 60 mg/kg of streptozotocin dissolved in 0.9% saline via the tail vein. Seven days after the injection the rats were diabetic having an average glucose concentration of 24.20 mM. 0.55 mmoles/kg of the ammonium salt of bis(maltolato)dioxovanadate suspended in 3% acacia was gavaged into the rats. Blood was collected and analyzed for glucose as a function of time. The table below shows that the compound was effective in reducing the elevated glucose levels.

| Time (hrs): | 0 | 1 | 2 | 4 | 8 | 12 | 24 |
|---|---|---|---|---|---|---|---|
| Glucose (mM): | 24.2 | 24.4 | 25.5 | 24.7 | 22.3 | 20.1 | 14.9 |

EXAMPLE 20

Preparation of Bis(ethylmaltolato)oxovanadium(IV), VO(ema)$_2$ [ETHYLBMOV]

To a mixture of VOSO$_4$.3H$_2$O (5 g, 23 mmol) and ethylmaltol (7 g, 50 mmol, PCI America Inc, Oregon), 150 mL H$_2$O (degassed by bubbling argon through it) was added under argon atmosphere. The suspension was refluxed and with rapid stirring, a solution of 15 mL NaOH (1.84 g, 46 mmol) was added dropwise over a period of 30 minutes. Refluxing was continued for another 30 minutes. The mixture was allowed to cool to ambient temperature and the dark green powder was isolated by filtration, washed with H$_2$O (3×10 mL) and diethyl ether (3×10 mL), and dried under high vacuum at ambient temperature. The yield was 7 g (89% based on VOSO$_4$.3H$_2$O).

IR (KBr): 991 cm$^{-1}$ (vv=o)

Elemental Analysis, Calc. (Found) for C$_{14}$H$_{14}$O$_7$V C 48.71 (48.80), H 4.09 (4.00)

Mass Spectrum (FAB$^+$): m/z=345 ([VO(ema)$_2$]$^+$)

UV-VIS (H$_2$O): $\lambda_{max}$(E)=440 nm (90M$^{-1}$ cm$^{-1}$)

Solid state magnetic moment: 1.72 BM (ambient temperature)

Isotropic ESR (H$_2$O): g$_o$=1.963; A$_c$=103.7 gauss.

EXAMPLE 21

Comparison of BMOV and ETHYLBMOV

Figure 8:
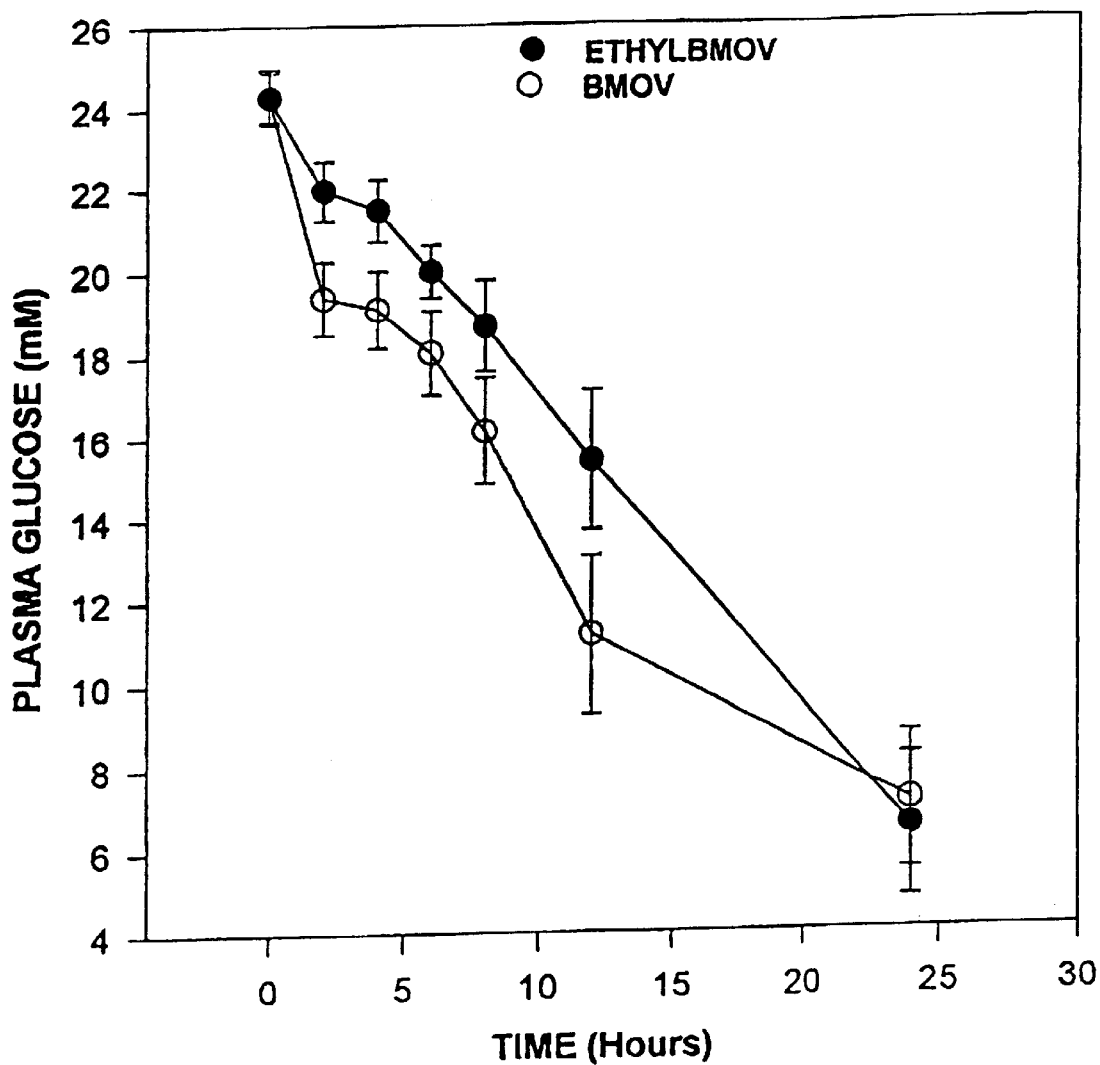
FIG. 8 shows a comparison of the effects of bis(maltolato)oxovanadium(IV) and bis(ethylmaltolato)oxovanadium(IV) on plasma glucose.
Figure 9:
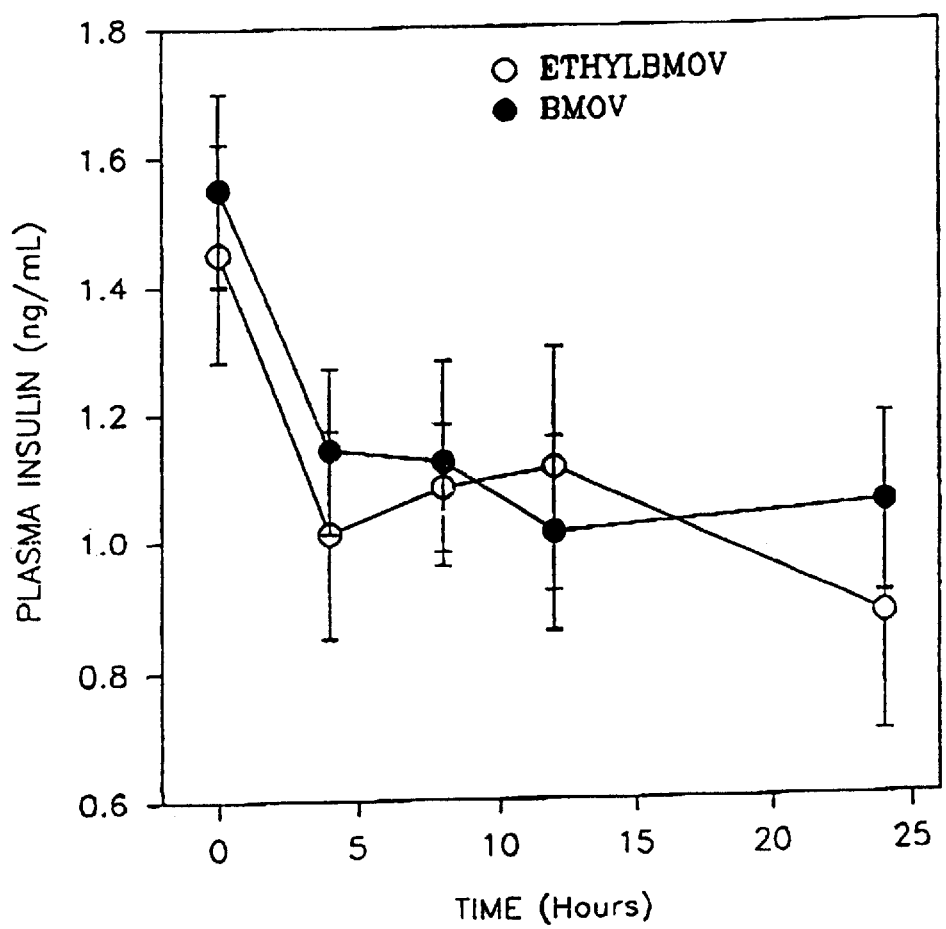
FIG. 9 shows a comparison of the effects of bis(maltolato)oxovanadium(IV) and bis(ethylmaltolato)oxovanadium(IV) on plasma insulin.

Animal studies were conducted in STZ-diabetic rats comparing doses of 0.6 mmol kg$^{-1}$ for VO(ma)$_2$ (BMOV) and VO(ema)$_2$ (ETHYLVMOV). FIGS. 8 and 9 respectively show plasma glucose and plasma insulin values recorded over 24 hour periods after one oral gavage of a water solution of either BMOV or ETHYLBMOV, in order to compare their efficacies. The differences are statistically insignificant.

The present invention provides a pharmaceutical composition useful for the treatment of diabetes (especially type II diabetes), as an appetite suppressant, or as an antihypertensive. The active compounds are absorbed across the gastrointestinal barrier and deliver the vanadyl ion to the bloodstream, where the insulin-mimetic properties of vanadium can be expressed. In contrast to insulin, the compositions are active when taken by mouth, and represent a significant advance in diabetes therapy. The compositions are also useful as orally active appetite suppressants and would be effective in treating obesity. The majority of diabetics are overweight, but obesity in general is a significant problem in western society, leading to an increase in morbidity and mortality. Morbid obesity is a health endangering condition. A drug that will suppress appetite, leading to weight loss, is of significant value. The active ingredients of the present invention are simple, monomeric species in the solid state. They are easily prepared, easily administered, relatively stable, and highly effective in lowering blood glucose, in suppressing appetite and in combatting hypertension.

We claim:

1. A method of treatment to lower elevated blood sugar levels in a mammal, said method comprising:
   administering to said mammal a pharmaceutical composition comprising:
   at least one physiologically acceptable carrier; and
   a physiologically tolerable vanadium complex of a bidentate monoprotic chelant, wherein said chelant is ethyl maltol;
   wherein said elevated blood sugar levels are lowered.

2. A method of treatment to lower elevated blood sugar levels in a mammal, said method comprising:
   administering to said mammal a pharmaceutical composition comprising:
   at least one physiologically acceptable carrier; and
   a physiologically tolerable vanadium complex of a bidentate monoprotic chelant capable of chelating vanadium to form a five- or six-membered unsaturated vanadium containing ring, said ring containing at least two further heteroatoms besides vanadium, and said ring if six-membered containing vanadium coordinating oxygen and nitrogen ring heteroatoms;
   wherein said elevated blood sugar levels are lowered.

3. A method as claimed in claim 2 further comprising the step of:
   administering a second physiologically tolerable antidiabetic drug.

4. A method as claimed in claim 3 wherein said second physiologically tolerable antidiabetic drug is insulin.

5. A method as claimed in claim 3 wherein said second physiologically tolerable antidiabetic drug is a compound incorporating metal ions other than the vanadium complex as recited in claim 2.

6. A method as claimed in claim 5 wherein said metal ion is chromium.

7. A method of treatment to lower elevated blood sugars levels in a mammal, said method comprising:
   administering to said mammal a pharmaceutical composition comprising:

at least one physiologically acceptable carrier; and a physiologically tolerable vanadium complex of a bidentate monoprotic chelant; wherein said chelant is an α-hydroxypyrone or α-hydroxypyridinone wherein said elevated blood sugar levels are lowered.

8. A method of treatment according to claim 7, wherein said pharmaceutical composition is a vanadium (III), (IV) or (V) complex.

9. A method of treatment according to claim 8, wherein said complex is an oxovanadium (IV) complex.

10. A method according to claim 7, further comprising the step of:

administering a second physiologically tolerable antidiabetic drug.

11. A method according to claim 10, wherein said second physiologically tolerable antidiabetic drug is insulin.

12. A method according to claim 10, wherein said second physiologically tolerable antidiabetic drug is a compound incorporating metal ions other than the vanadium complex as recited in claim 7.

13. A method according to claim 12, wherein said metal ion is chromium.

14. A method according to claim 7, wherein said administering step comprises oral administration.

15. A method according to claim 7, wherein said administering step comprises transdermal administration.

* * * * *

UNITED STATES PATENT AND TRADEMARK OFFICE
CERTIFICATE OF CORRECTION

PATENT NO: 5,888,993
DATED: March 30, 1999
INVENTOR(S): McNeill et al.

It is certified that error appears in the above-identified patent and that said Letters Patent is hereby corrected as shown below:

Title page, item[75], inventors:
*Replace the first named inventor's last name of "McNeil" with --McNeill--.*

Signed and Sealed this

Twenty-first Day of September, 1999

*Attest:*

Q. TODD DICKINSON

*Attesting Officer*  *Acting Commissioner of Patents and Trademarks*